US00RE44399E

(19) United States
(12) Reissued Patent
Keich et al.

(10) Patent Number: US RE44,399 E
(45) Date of Reissued Patent: *Jul. 30, 2013

(54) **ONE DOSE VACCINATION WITH *MYCOPLASMA HYOPNEUMONIAE***

(75) Inventors: Robin Lee Keich, Portage, MI (US); Lisa Grace Sabbadini, Mystic, CT (US)

(73) Assignee: Zoetis LLC, Florham Park, NJ (US)

( * ) Notice: This patent is subject to a terminal disclaimer.

(21) Appl. No.: 13/411,232

(22) Filed: Mar. 2, 2012

Related U.S. Patent Documents

Reissue of:
(64) Patent No.: 6,846,477
Issued: Jan. 25, 2005
Appl. No.: 10/174,701
Filed: Jun. 19, 2002

U.S. Applications:
(60) Provisional application No. 60/302,636, filed on Jul. 2, 2001.

(51) Int. Cl.
*A61K 49/00* (2006.01)
*A61K 39/38* (2006.01)

(52) U.S. Cl.
USPC ..... 424/9.1; 424/9.2; 424/93.1; 424/93.4; 424/184.1; 424/234.1; 424/264.1; 435/243; 435/870

(58) Field of Classification Search
None
See application file for complete search history.

(56) References Cited

U.S. PATENT DOCUMENTS 6,113,916 A * 9/2000 Bhogal et al. ..... 424/264.1

FOREIGN PATENT DOCUMENTS

| | | | |
|---|---|---|---|
| EP | 0 475 185 | A1 | 3/1992 |
| WO | WO 91/15593 | | 10/1991 |
| WO | WO 94/18627 | A1 | 12/1991 |
| WO | WO094/07531 | * | 4/1994 |
| WO | WO 94/07531 | A1 | 4/1994 |
| WO | WO 95/09870 | | 4/1995 |
| WO | WO 96/28472 | | 9/1996 |
| WO | WO 99/26664 | | 6/1999 |

OTHER PUBLICATIONS

Appay, Victor, Daniel C Douek &. David A Price. CD8+ T cell efficacy in vaccination and Disease. *Nature Medicine* (2008) 14 (6): 623-628.
Behn, Ulrich. Idiotypic networks: toward a renaissance? *Immunological Reviews* (2007) 216: 142-152.
Gerner, Wilhelm, Tobias Kaser, Armin Saalmuller. Porcine T lymphocytes and NK cells—An update. *Developmental and Comparative Immunology* (2009) 33; 310-320.
Langman, R. E. and M. Cohn. The 'complete' idiotype network is an absurd immune system. *Immunology Today* (1986) 7 (4):100-101.
Locksley, Richard M. Nine lives: plasticity among T helper cell subsets *J. Exp. Med.* (2009) 206 (8) 1643-1646.
Mosmann, Timothy R., Holly Cherwinski, Martha W. Bond, Martin A. Giedlin and Robert L. Coffman. Two Types Of Marine Helper T Cell Clone I. Definition According to Profiles of Lymphokine Activities and Secreted Proteins. *Journal of Immunology* (1986) 136 (7):2348.
Welters, Marij J.P., Martijn S. Bijker, Susan J.F. van den Eeden , Kees L.M.C. Franken, Cornelis J.M. Melief, Rienk Offringa, Sjoerd H. van der Burg. Multiple CD4 and CD8 T-cell activation parameters predict vaccine efficacy in vivo mediated by individual DC-activating agonists *Vaccine* 25 (2007) 1379-1389.
Seder, Robert A., Patricia A. Darrah and Mario Roederer. T-cell quality in memory and protection: implications for vaccine design. *Nature Reviews Immunoloy* vol. 8 pp. 247-259 (2008).
Uenishi, Hirohide, Hiroki Shinkai. Porcine Toll-like receptors: The front line of pathogen monitoring and possible implications for disease resistance. *Developmental and Comparative Immunology* 33 (2009) 353-361.
Zuckermann, FA and Gaskins, HR. Distribution of porcine CD4/CD8 double-positive T lymphocytes in mucosa-associated lymphoid tissues *Immunology* 1996 87;493-499.
Bandrick, Meggan, et al. Passive transfer of maternal *Mycoplasma hyopneumoniae*-specific cellular immunity to piglets; Clinical and vaccine immunology, Mar., vol. 15, No. 3 (2008) pp. 540-543.
Butler, John E, et al. Development of the neonatal B and T cell repertoire in swine: implications for comparative and veterinary immunology; Vet. Res. 37 (2006) pp. 417-441.
Francis, L. Black Response of young pigs to foot-and-mouth disease oil emulsion vaccination in the presence and absence of maternally derived neutralising antibodies, Research in Veterinary Science (1986), 41, pp. 33-39.
A. Bouma, et al. The influence of maternal immunity on the transmission of pseudorabies virus and on the effectiveness of vaccination; Vaccine, vol. 15, No. 3 pp. 287-294 (1997).
D. Klinkenberg, at al. Influence of maternal antibodies of efficacy of a subunit vaccine : Transmission of classical swine fever virus between pigs vaccinated at 2 weeks of age; Vaccine 20 (2002) pp. 3005-3013.
Terpstra C, Wensvoort G, Influence of the vaccine regimeon the har immune response for swine fever; Vet. Microbiol. (1987) PubMed Result.
Schwager, J. et al., Maturation of the mitogen responsiveness, and IL2 and IL6 production by neonatal swine leukocytes. Veterinary Immunology and Immunopathology, v. 57, 1997, pp. 105-119.
Butler, J.E. et al, The piglet as a model for B cell and immune system development, Veterinary Immunology and Immunopathology, v 128, 2009, pp. 147-170.
M. Okada et al., "Evaluation of *Mycoplasma hyopnemoniae* Inactivated Vaccine in Pigs under Field Conditions", J. Vet. Med. Sci. vol. 61(10), 1999, pp. 1131-1135.
P. Borghetti et al., *Effect of Weaning and Vaccinations on Immune and Hormonal Parameters in Neonatal Swine,* Veterinary Research Communications, v. 30 (suppl 1), 2006, pp. 227-230.
G.I. Solano-Aguitar et al., *Developmental Immunity in Neonatal Pigs Monitored by the Function of Peripheral Blood Mononuclear Cells,* Proceedings of the American Association of Swine Veterinarians 35th Annual Meeting, Mar. 5-8, 2005, Des Moines, Iowa, Paper.
C. Hammenberg et al., *Immunodeficiency in Young Pigs,* Am. J. Vet Res., vol. 50 (6), 1989, pp. 868-874.

(Continued)

*Primary Examiner* — Rodney P. Swartz
(74) *Attorney, Agent, or Firm* — White & Case LLP; Joel Silver; E. Victor Donahue

(57) ABSTRACT

The present invention relates to methods for treating or preventing a disease or disorder in an animal caused by infection by Mycoplasma hyopneumoniae (M. hyo) by administering to the animal at approximately three (3) to ten (10) days of age, a single dose of an effective amount of a M. hyo vaccine. The M. hyo vaccine can be a whole or partial cell inactivated or modified live preparation, a subunit vaccine, or a nucleic acid or DNA vaccine. The M. hyo vaccine administered in accordance with the present invention can be synthesized or recombinantly produced.

16 Claims, No Drawings

OTHER PUBLICATIONS

J.A. Roth, Chapter 56, "The Immune System", in Disease of Swine, Barbara E. Straw, eds., 8th edition, 1999, Iowa State/Blackwell Press.

Goodwin et al., Br. Vet. J. 129(5) pp. 456-464, 1973.

"The Influence of Passive Immunity on Serological Responses to *Mycoplasma hyopneumoniae* Vaccination", B. Thacker, et al., Proceedings of the 15th IPVS Congress, Birmingham, England (Jul. 5-9, 1998).

"Persistence of Passively Acquired Antibodies to *Mycoplasm hypopneumoniae* in a Swine Herd", C. Morris, et al., Preventive Veterinary Medicine, 21, pp. 29-41 (1994).

* cited by examiner

ONE DOSE VACCINATION WITH *MYCOPLASMA HYOPNEUMONIAE*

Matter enclosed in heavy brackets [ ] appears in the original patent but forms no part of this reissue specification; matter printed in italics indicates the additions made by reissue.

CROSS-REFERENCE TO RELATED APPLICATION

This application claims the priority from U.S. Provisional Application No. 60/302,636, filed on Jul. 2, 2001.

FIELD OF THE INVENTION

The present invention relates to methods for treating or preventing a disease or disorder in an animal caused by infection with Mycoplasma hyopneumoniae (M. hyo) by administering to the animal at approximately three (3) to ten (10) days of age, a single dose of an effective amount of a M. hyo vaccine. The M. hyo vaccine can be a whole or partial cell inactivated or modified live preparation, a subunit vaccine, or a nucleic acid or DNA vaccine. The M. hyo vaccine administered in accordance with the present invention can be synthetically or recombinantly produced.

BACKGROUND OF THE INVENTION

M. hyo is a bacterial pathogen that causes enzootic pneumonia in swine. Enzootic pneumonia is a chronic disease that results in poor feed conversion, stunted growth and predisposition to secondary pulmonary infections. M. hyo is easily transmitted through respiratory tract secretions and by sow-to-piglet transmission, and is highly prevalent on pig farms. Approximately 99% of US swine herds are infected, costing the swine industry about $300 million annually.

The majority of known vaccines against M. hyo have been based on adjuvanted inactivated whole cell preparations of M. hyo. In addition, vaccines based upon immunogenic polypeptides or proteins may be synthesized or prepared by cloning and recombinant expression of M. hyo genes. M. hyo genes capable of expressing such polypeptides or proteins in vivo may also be used as vaccines.

Examples of whole cell inactivated M. hyo vaccines include RESPISURE and STELLAMUNE, commercially available from Pfizer Inc., USA.

In addition, several recombinantly produced immunogenic polypeptides and proteins of M. hyo that may be useful as subunit vaccines have been described. International Patent Publication WO 96/28472 describes six protein antigen species of M. hyo at molecular weights of 46-48, 52-54, 60-64, 72-75, 90-94 and 110-114 kilodaltons, and discloses partial protein sequences of the 52-54, 60-64 and 72-75 kilodalton antigens and the full length nucleotide and amino acid sequences of the 46-48 kilodalton antigen.

The cloning of the gene encoding the M. hyo protein P46, i.e. p46, was also described by Futo et al. (1995; J. Bacteriol 177:1915-1917). The same group showed that the in vitro expressed gene product was useful in diagnosing antibody responses to M. hyo infections without cross reactivity to other Mycoplasma species (Futo et al., 1995, J. Clin. Microbiol. 33:680-683). The sequences and diagnostic uses of the p46 gene described by Futo et al. are further disclosed in European Patent Publication No. 0 475 185 A1.

Wise and Kim (1987, J. Bacteriol., 169:5546-5555) report that there are four integral membrane protein species in M. hyo, named p70, p65 (P65, supra), p50 and p44, and that the latter three are modified by covalent lipid attachments and induce a strong humoral immune response. The protective effects of the immune response were not investigated. The gene encoding the P65 protein has been cloned, and its sequences and uses in vaccines and diagnostics are described in U.S. Pat. No. 5,788,962.

International Patent Publication WO 91/15593 describes five proteins of M. hyo of apparent molecular weights of 105, 90, 85, 70 and 43 kilodaltons. A full length sequence of the gene encoding 85 kilodalton protein (protein C) was provided, as were partial nucleotide sequences encoding the other four proteins.

U.S. Pat. No. 5,252,328 to Faulds discloses amino terminal sequences of immunoreactive M. hyo proteins, the molecular weights of which are 36, 41, 44, 48, 64, 68, 74.5, 79, 88.5, 96 and 121 kilodaltons. Other proteins identified based on the electrophoretic mobilities but for which no protein sequences were disclosed had apparent molecular weights of 22.5, 34 and 52 kilodaltons. While U.S. Pat. No. 5,252,328 proposed the use of these proteins in vaccine formulations, no results of vaccine trials were reported.

International Patent Publication WO 95/09870 discloses biochemical methods for the purification of M. hyo adhesions, the mycoplasmal integral membrane proteins responsible for adhesion to the cilia of the host's upper respiratory epithelium. WO 95/09870 also proposes assays and uses for these proteins, for example in vaccines and diagnostics.

A research paper by King et al. (1997; Vaccine 15:25-35) disclosed Mhp1, a 124 kilodalton adhesin that is a strain variant of P97.

A 94 kilodalton variant of P97 was identified by Wilton et al. (1998, Microbiology 144:1931-1943). Additionally, the p97 gene was shown to be part of an operon that also encodes a second protein, termed P102, of a predicted molecular weight of approximately 102 kilodaltons (Hsu et al., 1998, Gene 214:13-23). Minion and Hsu suggest the use of P102 in vaccines in the international patent publication WO 99/26664 but do not report vaccine trials.

None of the known M. hyo vaccines have been described as effective in a single dose treatment of swine at approximately 3 to 10 days of age. Such a vaccine would eliminate the need for multiple dosing and thereby significantly decrease the costs and labor associated with the worldwide massive vaccination of swine herds. Thus, there is a need for an effective M. hyo vaccine that can be administered to swine in a single dose vaccination at from about 3 to about 10 days of age for protecting and preventing diseases or disorders caused by M. hyo.

SUMMARY OF THE INVENTION

The present invention provides a method of treating or preventing a disease or disorder in an animal caused by infection with Mycoplasma hyopneumoniae comprising administering to the animal at from about 3 to about 10 days of age, an effective amount of a single dose of a Mycoplasma hyopneumoniae vaccine.

The method of the present invention eliminates the necessity of additional doses in order to generate and/or maintain immunity against M. hyo. The present method of single (one) dose vaccination provides protection to both seronegative and seropositive pigs against challenge with virulent M. hyo. The method of the present invention is effective in treating or preventing the symptoms caused by infection by M. hyo, including, for example, preventing and reducing lung lesions in swine.

The method of the present invention encompasses administering to swine an effective amount of a single dose of a M. hyo vaccine, wherein the M. hyo vaccine comprises a whole or partial cell preparation, such as a bacterin or modified live preparation, a subunit vaccine, such as a subunit vaccine comprising one or more, M. hyo derived polypeptides or proteins, immunogenic fragments of such polypeptides or proteins, or one or more M. hyo genes encoding such proteins, polypeptides or immunogenic fragments which genes or nucleic acids are capable of being expressed in vivo. The M. hyo polypeptides, proteins, immunogenic fragments thereof and genes or nucleic acids provided in the M. hyo vaccine can be synthesized or recombinantly produced using techniques known in art.

The M. hyo vaccine administered in accordance with the present invention may include additional components, such as an adjuvant. Various adjuvants that may be used include those described herein and those known in the art.

DETAILED DESCRIPTION OF THE INVENTION

The present invention encompasses a method of treating or preventing a disease or disorder in an animal caused by infection with Mycoplasma hyopneumoniae comprising administering to the animal at from about 3 to about 10 days of age, an effective amount of a single dose of a Mycoplasma hyopneumoniae vaccine.

The single dose vaccination method of the present invention eliminates the necessity of administration of additional doses to swine in order to generate and/or maintain immunity against M. hyo.

For clarity of disclosure, and not by way of limitation, the detailed description of the invention is divided into the following subsections which describe or illustrate certain features, embodiments or applications of the invention.

In certain embodiments, the vaccines used in the method of the present invention comprise a partial or whole cell M. hyo inactivated preparation (bacterin) or modified live vaccine and a pharmaceutically acceptable carrier, or partial or whole cell M. hyo inactivated preparation (bacterin) or modified live vaccine and an adjuvant.

In other specific embodiments, the vaccines used in the method of the present invention comprise an immunogenic protein or polypeptide or fragment thereof and a pharmaceutically acceptable carrier, or an immunogenic protein or polypeptide or fragment thereof and an adjuvant.

Definitions and Abbreviations

The term "treating or preventing" with respect to a M. hyopneumoniae infection as used herein means to inhibit the replication of M. hyopneumoniae bacteria, to inhibit M. hyopneumoniae transmission, or to prevent M. hyopneumoniae from establishing itself in its host, and to alleviate the symptoms of the disease or disorder caused by M. hyopneumoniae infection. The treatment is considered therapeutic if there is a reduction in bacterial load, decrease in pulmonary infections and/or increase in food uptake and/or growth. The method of the present invention is, for example, effective in preventing or reducing lung lesions.

The term "M. hyo vaccine" as used herein refers to a vaccine useful in prevention or treating a disorder or disease caused by infection with M. hyo. The M. hyo vaccine can include any vaccine effective in treating or preventing infection in swine by M. hyo. The M. hyo vaccine that may be used in the present invention can include, for example, a whole or partial M. hyo cell preparation, inactivated or modified live vaccines, a subunit vaccine having one or more M. hyo derived polypeptides or proteins, or immunogenic fragments of such proteins or polypeptides, or one or more M. hyo genes or nucleic acids encoding for one or more M. hyo derived polypeptides or proteins, or immunogenic fragments thereof, and which genes or nucleic acids are capable of being expressed in vivo in swine. The M. hyo polypeptides, proteins, immunogenic fragments of such polypeptides and proteins, or M. hyo genes or nucleic acids can be synthesized or recombinantly produced using techniques known in the art. Preferably, the M. hyo vaccine used in the method of the present invention is a bacterin.

The term "animal" as used herein refers to all non-human animals, including mammals.

The term "pig" as used herein refers to piglets, swine, pigs, porcine, sows, gilts, barrows, boars and members of the Suidae family.

Preferably, the method of the present invention is applied to an animal which is a non-human mammal; most preferably, a pig.

The term "bacterin" as used herein refers to a preparation of inactivated whole or partial M. hyo cells suitable for use as a vaccine.

The term "effective amount" refers to an amount of M. hyo vaccine sufficient to elicit an immune response in the subject to which it is administered. The immune response may comprise, without limitation, induction of innate, cellular and/or humoral immunity.

Inactivated (Partial or Whole Cell) and Modified Live Vaccines

Methods for preparing conventional inactivated or modified live vaccines for used in the method of the present invention are known in the art.

M. hyo bacterins which can be employed in the present single dose vaccination method can be obtained from various publicly available sources. For example, M. hyo bacterins can be prepared from M. hyo isolates. Numerous M. hyo isolates are known to those skilled in the art and are available from, e.g., the American Type Culture Collection, 10801 University Boulevard, Manassas, Va. 20110-2209. These include for example: ATTC nos. 25095, 25617, 25934, 27714 and 27715.

M hyo isolates can also be obtained directly from naturally or experimentally infected porcine lung lesions using known techniques.

M. hyo isolates can be inactivated using a variety of known methods, e.g., treating the bacterial isolate with binary ethyleneimine (BEI) as described in U.S. Pat. No. 5,565,205, or inactivation with, for example, formalin, heat, BPL, irradiation or glutaraldehyde.

M. hyo bacterins suitable for use in the method of the present invention can also be obtained through various commercial sources. Such sources include but are not limited to bacterins marketed under the trade name RESPIFEND (Fort Dodge, American Home Products), HYORESP (Merial Ltd), M+PAC (Schering Plough), PROSYSTEM M (Intervet), INGLEVAC M (Boebringer), RESPISURE (Pfizer Inc.), or STELLAMUNE MYCOPLASMA (Pfizer Inc.).

Preferred sources of M. hyo bacterin for use in the method of the present invention are RESPISURE and STELLAMUNE MYCOPLASMA bacterins.

A particularly preferred source of M. hyo bacterin for use in the method of the present invention is RESPISURE-1 bacterin (Pfizer Inc.), containing strain P-5722-3 (NL 1042), acquired from Purdue University, USA.

Preferably, the strain P-5722-3 strain is inactivated with BEI and adjuvanted with a commercially available adjuvant, preferably, the AMPHIGEN adjuvant (Hydronics, USA). A preferred dose is about 2.0 ml. Preservatives conventionally used include merthiolate/EDTA. A carrier may be added, preferably, PBS. Preparation of modified live vaccines, such as by attenuation of virulent strains by passage in culture, is known in the art.

Subunit Vaccines

The method of the present invention can be practiced using subunit vaccines having purified M. hyo immunogenic proteins, polypeptides and immunogenic fragments of such proteins and polypeptides. Such proteins and polypeptides can be prepared using techniques known in the art. Further, methods which are well known to those skilled in the art can be used to determine protein purity or homogeneity, such as polyacrylamide gel electrophoresis of a sample, followed by visualizing a single polypeptide band on a staining gel. Higher resolution may be determined using HPLC or other similar methods well known in the art.

In a specific embodiment, the vaccine used in the present invention comprises at least one protein of M. hyo such as, but not limited to, P46, P65, P97, P102, P70, P50 and P44.

In other embodiments, the vaccine used in the method of the present invention comprises a M. hyo bacterin (inactivated whole or partial cell or modified live) or a M. hyo protein or polypeptide or immunogenic fragment thereof and at least one other immunogen (inactivated whole or partial cell or modified live) or an immunogenic or antigenic protein, polypeptide or immunogenic fragment thereof, and is preferably a viral, bacterial or parasitic polypeptide. Examples such of other pathogens and proteins, polypeptides or immunogenic fragments thereof include, but are not limited swine influenza virus (SIV), porcine reproductive and respiratory disease virus (PRRS or mystery swine disease), post-weaning diarrhea (PWD) and porcine proliferative enteritis (PPE). Such a composition is beneficial as a combination vaccine.

In a further specific embodiment, the immunogenic fragments of such proteins or polypeptides have a sequence comprising at least 10, at least 20, at least 30, at least 40, at least 50 or at least 100 contiguous amino acids of the immunogenic proteins and polypeptides used in the method of the present invention, including but not limited to P46, P65, P97, P102, P70, P50 and P44.

Further, the M. hyo proteins for use in vaccines are substantially pure or homogeneous. The method of the present invention uses proteins or polypeptides which are typically purified from host cells expressing recombinant nucleotide sequences encoding these proteins. Such protein purification can be accomplished by a variety of methods well known in the art. See, for example, the techniques described in "Methods In Enzymology", 1990, Academic Press, Inc., San Diego, "Protein Purification: Principles and practice", 1982, Springer-Verlag, New York.

Purified M. hyo polypeptides and proteins and immunogenic fragments thereof can also be prepared using known synthetic methods.

Vaccine Formulations

Suitable preparations of the vaccines used in the present invention include injectables, either as liquid solutions or suspensions; solid forms suitable for solution in, or suspension in, liquid prior to injection, may also be prepared. The preparation may also be emulsified. The active immunogenic ingredients are often mixed with adjuvants which are pharmaceutically acceptable and compatible with the active ingredient.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccine formulations used in the present invention comprise an effective immunizing amount of the M. hyo immunogen and a pharmaceutically acceptable carrier. Vaccine preparations comprise an effective immunizing amount of one or more antigens and a pharmaceutically acceptable carrier. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

Use of purified antigens as vaccine preparations can be carried out by standard methods. For example, the purified protein(s) should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin; glycosides, e.g., saponin and saponin derivatives such as Quil A or GPI-0100; cationic surfactants, e.g. DDA (quaternary hydrocarbon ammonium halogenides, pluronic polyols; polyanions and polyatomic ions; polyacrylic acids, non-ionic block polymers, e.g., Pluronic F-127 (B.A.S.F., USA); Avridine and Rantidine; peptides; recombinant mutant labile toxins, e.g., leukotoxin (rmLT) or cholera toxin (CT); chemically bound or close proximity molecular transporters; mineral oils, e.g. Montanide ISA-50 (Seppic, Paris, France), carbopol, Amphigen (Hydronics, USA), Omaha, Nebr. USA, Alhydrogel, (Superfos Biosector, Frederikssund, Denmark) oil emulsions, e.g. an emulsion of mineral oil such as BayolF/Arlacel A and water, or an emulsion of vegetable oil, water and an emulsifier such as lecithin; alum, MDP, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine; cholesterol cytokines and combinations of adjuvants. Polyatomic ions can also function as dispersing, thickening and anticaking agents which allow the vaccine to be resuspended as a mondisperse suspension after a prolonger period of settling. The adjuvant combinations may be presented in aqueous, encapsulated (controlled or delayed release) or microencapsulated forms The immunogen may also be incorporated into liposomes, or conjugated to polysaccharides and/or other polymers for use in a vaccine formulation In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Gene and Nucleic Acid Vaccines

The method of the present invention can be practiced using M. hyo genes or nucleic acids encoding for immunogenic proteins, polypeptides and immunogenic fragments of such proteins and polypeptides. Such genes and nucleic acids can be expressed in vivo and can be prepared using techniques known in the art.

In a specific embodiment, the vaccine used in the present invention comprises at least one gene or nucleic acid encoding for a protein of M. hyo such as, but not limited to, P46, P65, P97, P102, P70, P50 and P44.

In a further specific embodiment, the genes or nucleic acids used in the method of the present invention encode for the immunogenic fragments of the M. hyo proteins or polypeptides have a sequence comprising at least 10, at least 20, at least 30, at least 40, at least 50 or at least 100 contiguous amino acids of the immunogenic proteins and polypeptides used in the method of the present invention, including but not limited to P46, P65, P97, P102, P70, P50 and P44.

In other embodiments of the method of the present invention, the gene or nucleic acids used are administered by known methods, such as, for example, by use of a gene gun.

In yet other embodiments of the method of the present invention, the gene or nucleic acids used are DNA vaccines. Further, the nucleic acid or genes can be present in association with liposomes or other transfection facilitating agents, as are known in the art.

Methods for the preparation and delivery of DNA vaccines are known in the art. See, for example, Krishnan, B. R, "Current Status of DNA vaccines in veterinary medicine", Advanced Drug Delivery Reviews, Elsevier Science (2000).

Expression Systems

A variety of host-expression vector systems may be utilized to express the antigenic protein sequences of the invention. Such host-expression systems represent vehicles by which the coding sequences of interest may be produced and subsequently purified, but also represent cells which may, when transformed or transfected with the appropriate nucleotide coding sequences, exhibit the M. hyo gene products used in the method of the present invention in situ. These include but are not limited to microorganisms such as bacteria (e.g., E. coli, B. subtilis) transformed with recombinant bacteriophage DNA, plasmid DNA or cosmid DNA expression vectors containing mhp3 coding sequences; yeast (e.g., Saccharomyces, Pichia) transformed with recombinant yeast expression vectors containing the M. hyo gene product coding sequences; insect cell systems infected with recombinant virus expression vectors (e.g., baculovirus) containing the M. hyo coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing M. hyo coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter). In a preferred embodiment, the expression system is a bacterial system.

M. hyopnuemoniae polypeptides and proteins and immunogenic fragments thereof can also be expressed and delivered using live recombinant viral and bacterial vectors such as adenovirus or Salmonella. The actual vectors are also known and readily available within the art or can be constructed by one skilled in the art using well-known methodology.

Dosing and Modes of Administration

According to the present invention, a single dose of an effective amount of a M. hyo vaccine administered to swine of approximately 3 to 10 days of age provides effective immunity against a later challenge of M. hyo. Preferably, the M. hyo vaccine is administered at about six to about eight days of age. Most preferably, the M. hyo vaccine is administered at about seven days of age.

The amount of a M. hyo bacterin vaccine effective in one dose administration contains about $1\times10^6$ to about $5\times10^{10}$ color changing units (CCU) per dose. Preferably, a M. hyo bacterin vaccine that provides effective immunity in a single dose contains about $1\times10^8$ to $5\times10^{10}$ CCU/dose and more preferably, about $5\times10^8$ to $5\times10^{10}$ CCU/dose.

According to the present invention, when the preferred bacterin product RESPISURE-1 is administered, the amount of the RESPISURE-1 bacterin for one dose administration is about 0.5 to about 3.0 ml, preferably about 1.5 ml to about 2.5 ml, and more preferably, about 2 ml.

The amount of a M. hyo vaccine which is a vaccine comprising one or more M. Hyo genes or nucleic acids (preferably DNA) encoding for immunogenic proteins or polypeptides or immunogenic fragments of such proteins or polypeptides effective in the method of the present invention is from about 0.1 g to about 200 mg.

In accordance with the present invention, administration can be achieved by known routes, including the oral, intranasal, mucosal topical, transdermal, and parenteral (e.g., intravenous, intraperitoneal, intradermal, subcutaneous or intramuscular). Administration can also be achieved using needle-free delivery devices. Administration can be achieved using a combination of routes, e.g., first administration using a parental route and subsequent administration using a mucosal route. A preferred route of administration is intramuscular administration.

Effective doses (immunizing amounts) of the vaccines of the invention may also be extrapolated from dose-response curves derived from model test systems.

The present vaccination methods provide protective immunity for both piglets seropositive and piglets seronegative for M. hyo. Seropositive piglets refer to those piglets which have in the serum, antibodies against M. hyo. Seronegative piglets refer to those piglets which do not have in the serum, detectable levels of antibodies against M. hyo.

The present invention is further illustrated, but not limited by the following examples.

EXAMPLE 1

Preparation of a M. hyo Bacterin

BinaryEthylenelmine (BEI) is used for inactivation of M. hyo strain NL1042.

At the end of the growth period, the pH of the culture was raised to 7.8±0.2, and the pH was maintained within this range for at least one hour. At this time, a filter sterilized aqueous solution of 2-BromoEthylAminehydrobromide (BEA) was added to a final concentration of approximately 4.0 mM. In the presence of the elevated pH, the BEA is chemically changed to BEI. The culture was incubated at 37±2° C. with constant agitation for at least 24 hours.

After the 24 hours incubation, a filter sterilized aqueous solution of sodium thiosulfate was added to a final concentration of approximately 4 mM to neutralize excess BEI. The culture was incubated at 37±2° C. with constant agitation for an additional 24 hours.

Following inactivation, but prior to neutralization with sodium thiosulfate, a representative sample was taken and tested for completion of inactivation. Fresh medium containing 0.0026% phenol red was inoculated with a 5-20% inoculum and incubated at 37±2° C. for at least one week prior to examination for a color change, which is indicative of failure to inactivate. Bulk samples were tested for sterility in thioglycollate broth at 37±2° C., and trypticase soy broth at room temperature. The inactivated culture may be transferred into sterile storage vessels and stored at 2-8° C. until assembled.

Potency was determined by an in vitro serological assay to quantitiate antigen in the final container. The potency of the vaccines used in the efficacy study determines the minimum potency that must be present in the vaccine at the date of expiration.

Bulk or final container samples of completed product of each serial or first subserial was tested for M. hyo as follows.

The bacterin was stored at 50° C. in 100 ml vials. The vials were thawed and sub-aliquots of 15 mL are stored at 5° C.+/−2° C. until used.

To test the potency of an assembled serial, a sample of the serial was compared to a reference, and RP units are determined for the serial. A serial or subserial should preferably contain at least 6.33 RP at the initiation of dating, and at least 5.06 RP throughout dating.

RP refers to relative potency. The RP's can be determined by a relative antigen quantitation as compared to a reference vaccine. In this case the reference has an RP by definition=1.0. The single dose product of the present invention preferably has a RP of 6.33, that is 6.33 times the reference.

Merthiolate is added as a preservative in a final concentration not to exceed 0.01% (w/v).

10% Ethylene-Diamine Tetra Acetic acid (EDTA, Disodium or tetrasodium salt) solution is added as preservative in a final concentration of approximately 0.07% (w/v).

EXAMPLE 2

Animals

Pigs approximately one week of age were selected for vaccination. Serological status to M. hyo were assessed in an ELISA assay. Pigs with an ELISA value≦0.50 were considered M. hyo negative. Pigs with an ELISA value of greater than 0.50 were considered serologically positive for M. hyo.

Vaccines

M. hyo bacterin RESPISURE-1 (Pfizer Inc.), was used to vaccinate pigs. The potency of the vaccine was determined prior to use by relative antigen quantitation as compared to a reference M. hyo bacterin. The reference vaccine (RP=1.0) contained about 8000 units of antigen (about 1 to $2\times10^8$ CCU of viable cells harvested prior to inactivation) per dose, determined by a solid phase immunoassay which measured the quantity of M. hyo antigen in the vaccine.

The same liquid adjuvant (AMPHIGEN) used in formulating RESPISURE-1 was used as the placebo (i.e., without bacterial cells).

Challenge Inoculum

The challenge inoculum, was provided as 10 ml aliquots of lung homogenate, frozen at −70° C., and was identified as a derivative of M. hyo strain 11 (L1 36). The inoculum was thawed and then diluted in Friis Mycoplasma Broth to achieve a 1:25 dilution, and kept on ice until administered. Each pig received a 5 ml intranasal dose (2.5 ml per nostril) of the 1:25 suspension on days specified in each of the following examples. On each day of challenge, an aliquot of the lung inoculum was cultured to confirm the absence of bacterial contamination. A second aliquot was back titrated on each of the 3 days, the results indicated that the inoculum contained approximately $10^6$-$10^7$ color changing units (CCU)/ml of M. hyo.

Experimental Procedure

Pigs were identified with ear tags while they were still on the sow [Day (−1)]. The pigs were allotted to pens and treatment groups according to a generalized random block design. Pigs were blocked based on litter and post-weaning pen.

On Day 0, pigs were vaccinated with either a 2 ml intramuscular dose of M. hyo bacterin RESPISURE-1 (Pfizer Inc.), or with a 2 ml intramuscular dose of placebo. Each pig received a 5 ml intranasal dose of the 1:25 suspension of the challenge inoculum on days specified in each of the following examples. All pigs were monitored and checked for signs of clinical disease daily.

At a specified time after the first day of challenge, all pigs were euthanized and necropsied. The lungs were removed and evaluated. The post-mortem examination included an estimate of the extent of pathology associated with mycoplasmal respiratory disease. Each lung lobe was examined, and lesions were sketched to estimate the percent involvement of each lobe. The degree of gross lesions present was recorded.

Data Analysis

Efficacy was evaluated based on percent of lung lesions typical of a M. hyo infection. Pigs in a treatment group (vaccinates) were determined to have a percentage of total lung with lesions that was significantly (P≦0.05) less than pigs in the placebo group.

Percentage of Total Lung with Lesions

Percent gross involvement per each lung lobe was weighted using the following ratios of individual lung lobes to total lung mass: left cranial 10%, left middle 10%, left caudal 25%. right cranial; 10%, right middle 10%, right caudal 25%, and accessory 10%. The weighted lung lobe values were then summed across lobes to yield the Percentage of Total Lung with Lesions (Pointon et al., 1992).

EXAMPLE 3

Protection against challenge with virulent M. hyo was evaluated in pigs serologically positive for M. hyo using a single dose of M. hyo bacterin RESPISURE-1 (Pfizer Inc), administered to pigs at 3 to 8 days of age.

Five replicate potency assays for RESPISURE-1 were conducted at or around the time of vaccination. The relative potency (RP) was determined by relative antigen quantitation as compared to a reference vaccine. The reference vaccine, having a RP=1.0, contained about 8000 units of M. hyo antigen. The RPs from these five assays were 5.42, 3.96, 4.71, 5.49 and 4.36, respectively.

On Day 0, pigs in Treatment Group T02 (see Table 1 below) were vaccinated with a 2 ml intramuscular dose of M. hyo bacterin RESPISURE-1 (Pfizer Inc.). Pigs in Group T01 were vaccinated intramuscularly with 2 ml of a placebo. Each pig received a 5 ml intranasal dose of the 1:25 suspension of the challenge inoculum on Days 178, 179 and 180. On each of the 3 days, an aliquot of the challenge material was cultured at time of inoculation to confirm the absence of bacterial contamination. A second aliquot was back-titrated to confirm the challenge stock contained approximately $10^7$ CCU/mL of M. hyo. All pigs were monitored and checked for signs of clinical disease daily.

Thirty days after the first day of challenge, all pigs were euthanized and necropsied. The lungs were removed and evaluated. The post-mortem examination included an estimate of the extent of pathology associated with mycoplasmal respiratory disease. Each lung lobe was examined, and lesions were sketched to estimate the percent involvement of each lobe. The degree of gross lesions present was recorded

TABLE 1

| Treatment Group | Vaccination Compound | Number | Vaccinated Day 0 | Challenge Day 178[1] | Challenge Day 179[1] | Challenge Day 180[1] |
|---|---|---|---|---|---|---|
| T01 | Placebo | 26 | 26 | 26 | 26 | 26 |
| T02 | Vaccine | 26 | 26 | 24[2] | 22[3] | 22[3] |

[1]Virulent *M. hyo* inoculum
[2]Pigs 71 and 73 were removed from the study prior to challenge because both animals lost all ear tags and therefore the identity of each animal could not be determined.
[3]Pig 36 found dead on Day 178 due to anesthetic complications. Pig 31 was found dead on Day 179 due to anesthetic complications.

Lung lesion results are summarized in Table 2. The results indicated that vaccinated pigs (T02) had significantly (P=0.0385) lower least squares mean percentage of pneumonic lung lesions than placebo pigs (T01) (2.0 vs. 4.5%).

TABLE 2

Summary of Percentage of Total Lung Lesions

| Treatment | Compound | Number of Pigs | LS Mean | Range |
|---|---|---|---|---|
| T01 | Placebo | 26 | $4.5^a$ | 0 to 36.75 |
| T02 | Vaccine | 22 | $2.0^b$ | 0 to 13.75 |

[a,b]Values with a different superscript are statistically significant (P = 0.0385)

The results indicate that single vaccination of pigs at approximately one week of age with M. hyo bacterin RESPISURE-1, induced protection against a subsequent challenge with virulent M. hyo.

EXAMPLE 4

Protection against challenge with virulent M. hyo was evaluated in pigs serologically negative for M. hyo using a single dose of M. hyo bacterin RESPISURE-1, administered to pigs at 3 to 8 days of age.

Five replicate potency assays for the vaccine were conducted at or around the time of vaccination. The RP was determined by a relative antigen quantitation as compared to a reference vaccine. The reference vaccine, having a RP=1.0, contained about 8000 units of M. hyo antigen. The RP's from these five assays were 5.42, 3.96, 4.71, 5.49 and 4.36, respectively.

On Day 0, pigs in Treatment Group T02 were vaccinated with a 2 ml intramuscular dose of M. hyo bacterin RESPISURE-1. Pigs in Group T01 were vaccinated intramuscularly with 2 ml of a placebo. Each pig received a 5 mL intranasal dose of the 1:25 suspension of the challenge inoculum on Days 173, 174 and 175. On each of the 3 days, an aliquot of the challenge material was cultured at time of inoculation to confirm the absence of bacterial contamination. A second aliquot was back-titrated to confirm the challenge stock contained approximately $10^6$ CCU/ml of M. hyo. All pigs were monitored and checked for signs of clinical disease daily.

Twenty-nine days after the first day of challenge, all pigs were euthanized and necropsied. The lungs were removed and evaluated. The post-mortem examination included an estimate of the extent of pathology associated with M. hyo induced respiratory disease. Each lung lobe was examined, and lesions sketched to estimate the percent consolidation in each lobe. The degree of gross lesions present was recorded.

Table 3 summarizes the experimental design.

TABLE 3

| Treatment Group | Vaccination Compound | Number | Vaccinated Day 0 | Challenge Day 173[1] | Challenge Day 174[1] | Challenge Day 175[1] |
|---|---|---|---|---|---|---|
| T01 | Placebo | 26 | 26 | 25[2] | 24[4] | 24 |
| T02 | Vaccine | 26 | 26 | 23[3] | 20[5] | 20 |

[1]Virulent *M. hyo.*
[2]Pig 123 was euthanized on Day 19 due to chronic septic polyarthritis.
[3]Pig 222 was found dead on Day 40. Necropsy revealed a large amount of pericardial fluid and hemorrhage on epicardium. Pig 102 was euthanized on Day 95 due to a rectal prolapse. Pig 204 was found dead on Day 145. No necropsy was performed due to advanced carcass decomposition.
[4]Pig 244 was found dead on Day 174 following the first day of challenge due to anesthetic complications.
[5]NEEA to account for 3 pigs Lung lesion results are summarized in Table 4. Overall analysis indicated that vaccinated pigs (T02) had a significantly (P=0.0001) lower least squares mean percentage of pneumonic lung lesions than placebo pigs (T01) (0.3 vs. 5.9%).

TABLE 4

Summary of Percentage of Total Lung Lesions
Percent of Lung with Lesion

| Treatment | Compound | Number of Pigs | LS Mean | Range |
|---|---|---|---|---|
| T01 | Placebo | 24 | $5.9^a$ | 0 to 36 |
| T02 | Vaccine | 20 | $0.3^b$ | 0 to 6 |

[a,b]Values with different superscripts are statistically different (P = 0.0001).

The results of this study indicate that single vaccination of pigs with M. hyo bacterin RESPISURE ONE induced protection against a subsequent experimental challenge with virulent M. hyo.

EXAMPLE 5

Protection against challenge with virulent M. hyo was evaluated in pigs serologically negative for M. hyo using a single dose of M. hyo bacterin RESPISURE-1 administered to pigs at 3 to 8 days of age. Five replicate potency assays for the bacterin were conducted at or around the time of vaccination. The RP was determined by a relative antigen quantitation as compared to a reference vaccine. The reference vaccine, having a RP=1.0, contained about 8000 units of M. hyo antigen. The RP's from these five assays were 5.42, 3.96, 4.71, 5.49 and 4.36, respectively.

On Day 0, pigs in Treatment Group T02 were vaccinated with a 2 ml intramuscular dose of M. hyo bacterin. Pigs in Group T01 were vaccinated intramuscularly with 2 ml of a placebo. Each pig received a 5 ml intranasal dose (2.5 ml per nostril) of the 1:25 suspension of the challenge inoculum on Days 76, 77 and 78. On each of the 3 days, an aliquot of the challenge material was cultured at time of inoculation to confirm the absence of bacterial contamination. A second aliquot was back-titrated to confirm the challenge stock contained approximately $10^6$ CCU/mL of M. hyo. All pigs were monitored and checked for signs of clinical disease daily.

Twenty-nine days after the first day of challenge, all pigs were euthanized and necropsied. The lungs were removed and evaluated. The post-mortem examination included an estimate of the extent of pathology associated with M. hyo induced respiratory disease. Each lung lobe was examined, and lesions sketched to estimate the percent involvement in each lobe. The degree of consolidation present was recorded.

Table 5 summarizes the experimental design.

TABLE 5

| Treatment Group | Vaccination Compound | Number | Vaccinated Day 0 | Challenge Day 176[1] | Challenge Day 177[1] | Challenge Day 178[1] |
|---|---|---|---|---|---|---|
| T01 | Placebo | 26 | 26 | 23[2] | 23 | 23 |
| T02 | Vaccine | 26 | 26 | 21[3] | 21 | 21 |

[1]Virulent *M. hyo* inoculum

[2]Pigs 237 and 239 tested positive on Day-1 for *M. hyo* pnuemoniae. These piglets were removed from the study on Day 14 and euthanized. Pig 220 was found dead on Day 3 due to being crushed by the sow.

[3]Pigs 238, 240 and 277 tested positive on Day-1 for *M. hyo* pneumoniae. These piglets were removed from the study on Day 14 and euthanized. Pig 280 was euthanized on Day 7 after being anorexic and unthrifty. Pig 177 was euthanized on Day 40 due to chronic wasting syndrome.

Lung lesion results are summarized in Table 6. The overall analysis indicated that vaccinated pigs (T02) had a significantly (P=0.0001) lower least squares mean percentage of pneumonic lung lesions than placebo pigs (T01) (0.5 vs. 9.9%).

TABLE 6

Summary of Percentage of Total Lung Lesions
Percent of Lung with Lesion

| Treatment | Compound | Number of Pigs | LS Mean | Range |
|---|---|---|---|---|
| T01 | Placebo | 23 | 9.9[a] | 0 to 40.5 |
| T02 | Vaccine | 21 | 0.5[b] | 0 to 5 |

[a,b]Values with different superscripts are statistically different (P = 0.0001).

What is claimed is:

[1. A method of treating or preventing a disease or disorder in an animal caused by infection with Mycoplasma hyopneumoniae (M. hyopneumoniae) comprising administering to the animal at from about 3 to about 10 days of age, an effective amount of a single dose of a Mycoplasma hyopneumoniae vaccine, wherein said M. hyopneumoniane vaccine comprises an inactivated M. hyopneumoniane whole cell preparation and wherein said single dose of the M. hyopneumoniane vaccine contains at least about $1\times10^8$ color changing units (CCU).]

[2. The method according to claim 1 wherein the animal is a pig.]

[3. The method according to claim 2, wherein said swine is seropositive for Mycoplasma hyopneumoniae.]

[4. The method according of claim 2, wherein said swine is seropositive for Mycoplasma hyopneumoniae.]

[5. The method according of claim 2, wherein said swine are protected up to 25 weeks following vaccination.]

[6. The method of claim 1, wherein the single dose of the M. hyopneumoniae vaccine contains from about $1\times10^8$ to $5\times10^{10}$ color changing units (CCU) per dose.]

[7. The method of claim 6 wherein the single dose of the M. hyopneumoniae vaccine contains from about $5\times10^8$ to $5\times10^{10}$ color changing units (CCU) per dose.]

[8. The method of claim 1 wherein the amount of said vaccine administered is from about 0.5 to about 3.0 ml.]

[9. The method of claim 1 wherein the amount of said vaccine administered is from about 1.5 ml to about 2.5 ml.]

[10. The method of claim 1 wherein the amount of said vaccine administered is about 2 ml.]

[11. The method of claim 1 wherein the Mycoplasma hyopneumoniae cell preparation is RESPISURE-1.]

[12. The method of claim 1 wherein the Mycoplasma hyopneumoniae vaccine further comprises a viral or bacterial antigen other than Mycoplasma hyopneumoniae.]

[13. The method of claim 12 wherein the said viral or bacterial antigens are selected from swine influenza virus (SIV), porcine reproductive and respiratory disease virus (PRRS or mystery swine disease), post-weaning diarrhea (PWD) and porcine proliferative enteritis (PPE).]

[14. The method according to claim 1 wherein said Mycoplasma hyopneumoniae preparation is administered intramuscularly.]

[15. The method according to claim 1 wherein the Mycoplasma hyopneumoniae vaccine further comprises an adjuvant.]

[16. The method according to claim 15 wherein the adjuvant is selected from the group consisting of: mineral gels; surface active substances such as lysolecityhin; glycosides comprising saponin or, saponin derivatives such as Quil A or GP1-0100; pluronic polyols; polyanions; non-ionic block polymers, mineral oils, oil emulsions, an emulsion of vegetable oil, water and an emulsifier such as lecithin; alum, cytokines, CpG oligonucleotides, and MDP, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-*hydroxyphosphoryloxy*)-*ethylamine*; *rm*LT, *and* AMPHIGEN.]

[17. The method according to claim 1 wherein the Mycoplasma hyopneumoniae further comprises a pharmaceutically acceptable carrier.]

*18. A method of treating or preventing a disease or disorder in a pig caused by infection with Mycoplasma hyopneumoniae (M. hyopneumoniae) consisting essentially of administering to the pig at from about 3 to about 10 days of age, an effective amount of a single dose of an M. hyopneumoniae vaccine which induces protective immunity in both seropositive pigs and seronegative pigs, said M. hyopneumoniae vaccine comprising an inactivated M. hyopneumoniae whole cell preparation and wherein said single dose of the M. hyopneumoniae vaccine contains at least about $1\times10^8$ color changing units (CCU).*

*19. The method according to claim 18, wherein said pig is seropositive for Mycoplasma hyopneumoniae.*

*20. The method according to claim 18, wherein said pig is seronegative for Mycoplasma hyopneumoniae.*

*21. The method according to claim 18, wherein said pig is protected up to 25 weeks following vaccination.*

*22. The method of claim 18, wherein the single dose of the M. hyopneumoniae vaccine contains from about $1\times10^8$ to $5\times10^{10}$ color changing units (CCU) per dose.*

*23. The method of claim 22 wherein the single dose of the M. hyopneumoniae vaccine contains from about $5\times10^8$ to $5\times10^{10}$ color changing units (CCU) per dose.*

*24. The method of claim 18 wherein the amount of said vaccine administered is from about 0.5 to about 3.0 ml.*

*25. The method of claim 18 wherein the amount of said vaccine administered is from about 1.5 ml to about 2.5 ml.*

*26. The method of claim 18 wherein the amount of said vaccine administered is about 2 ml.*

*27. The method of claim 18 wherein the Mycoplasma hyopneumoniae cell preparation is RESPISURE-1.*

*28. The method of claim 18 wherein the Mycoplasma hyopneumoniae vaccine further comprises a viral or bacterial antigen other than Mycoplasma hyopneumoniae.*

*29. The method of claim 28 wherein the said viral or bacterial antigens are selected from swine influenza virus (SIV), porcine reproductive and respiratory disease virus (PRRS or mystery swine disease), post-weaning diarrhea (PWD) and porcine proliferative enteritis (PPE).*

*30. The method according to claim 18 wherein said Mycoplasma hyopneumoniae preparation is administered intramuscularly.*

*31. The method according to claim 18 wherein the Mycoplasma hyopneumoniae vaccine further comprises an adjuvant.*

*32. The method according to claim 31 wherein the adjuvant is selected from the group consisting of: mineral gels; surface active substances such as lysolecithin; glycosides comprising saponin or, saponin derivatives such as Quil A or GP1-0100; pluronic polyols; polyanions; non-ionic block polymers, mineral oils, oil emulsions, an emulsion of vegetable oil, water and an emulsifier such as lecithin; alum, cytokines, CpG oligonucleotides, and MDP, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine; rmLT, and AMPHIGEN.*

*33. The method according to claim 18 wherein the Mycoplasma hyopneumoniae vaccine further comprises a pharmaceutically acceptable carrier.*

* * * * *